United States Patent
Knudsen et al.

(10) Patent No.: US 7,456,319 B2
(45) Date of Patent: Nov. 25, 2008

(54) PARA-ALKYLATION OF AROMATIC PRIMARY AMINES

(75) Inventors: George A Knudsen, Scotch Plains, NJ (US); Richard H. Schlosberg, Bridgewater, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 139 days.

(21) Appl. No.: 11/296,997

(22) Filed: Dec. 8, 2005

(65) Prior Publication Data

US 2006/0161021 A1 Jul. 20, 2006

Related U.S. Application Data

(60) Provisional application No. 60/644,947, filed on Jan. 19, 2005.

(51) Int. Cl.
*C07C 209/68* (2006.01)
(52) U.S. Cl. ...................................... 564/409
(58) Field of Classification Search ................. 564/307, 564/308, 409; 558/416
See application file for complete search history.

(56) References Cited

U.S. PATENT DOCUMENTS

| | | | |
|---|---|---|---|
| 3,649,693 | A | 3/1972 | Napolitano |
| 3,923,892 | A | 12/1975 | Klopfer |
| 4,128,582 | A | 12/1978 | Governale et al. |
| 4,436,936 | A | 3/1984 | Howell |
| 4,740,620 | A | 4/1988 | Dixon et al. |
| 4,760,184 | A | 7/1988 | Pierantozzi |
| 4,876,377 | A | 10/1989 | Agrawal et al. |
| 4,892,974 | A | 1/1990 | Burgoyne, Jr. et al. |
| 5,068,435 | A | 11/1991 | Burgoyne, Jr. et al. |

FOREIGN PATENT DOCUMENTS

| | | |
|---|---|---|
| EP | 0 240 018 A2 | 10/1987 |
| EP | 0 265 932 B1 | 1/1993 |
| GB | 846226 | * 10/1960 |

OTHER PUBLICATIONS

Engelhard Specification Sheet Grade F-22 Activated Adsorbent, Rev. 16 Nov. 1993.

* cited by examiner

*Primary Examiner*—Daniel M. Sullivan
*Assistant Examiner*—Yate' K Cutliff
(74) *Attorney, Agent, or Firm*—P. E. Purwin

(57) ABSTRACT

A method is provided for producing primarily para alkyl aromatic amines by alkylating a primary aromatic amine with an olefin in the presence of an acid activated clay.

8 Claims, No Drawings

PARA-ALKYLATION OF AROMATIC PRIMARY AMINES

This application claims the benefit of U.S. Application No. 60/644,947 filed Jan. 19, 2005.

FIELD OF THE INVENTION

The present invention relates to the nuclear alkylation of aromatic amines. More particularly, the invention relates to improvements in the production of p-alkyl aromatic amines.

BACKGROUND OF THE INVENTION

As is well known, para-alkyl primary aromatic amines in addition to being useful as chemical intermediates are also useful in a variety of other applications. For examples, they are used in lubricants as antioxidants and in fuels as antiknock agents, to mention a few.

Methods for alkylating primary aromatic amines typically result in the formation primarily of the ortho and meta isomers of the alkyl aromatic amines along with N-alkylated species. Although the ortho and meta isomers have somewhat similar properties to the para-isomers, most often the properties of the para-isomers are significantly better than the others making the para-isomer the compound of choice in many applications. Consequently attempts have been made to produce para-alkylated aromatic amines in preference to the ortho and meta compounds. In this regard mention is made of British Patent 846,226 and Canadian Patent 663,698 each of which disclose processes that result in the formation of mixtures relatively high in para alkylated phenyl amines. For example, in the alkylation of aniline with isobutylene by the process of British Patent 846,226 the p-tertiary butylaniline is obtained (about 85 to 88% based on moles of aniline converted) with varying amounts of o-tertiary butylaniline, N-tertiary butylaniline and di-tertiary butylaniline. In the process of Canadian Patent 663,698 the alkylation of aniline with isobutylene was reported as producing significant amount of di-tertiary butylaniline along with the para-tertiary butylaniline.

One object of the present invention is to provide an improved method in forming para alkylated primary aromatic amines.

Another object of the present invention is to provide a method for alkylating primary aromatic amines which favors the formation of the para alkylated derivative.

Another object of the present invention is to provide a method for forming para-alkylated primary aromatic amines in increased yields.

Other objects of the invention will become apparent from the description hereinafter.

SUMMARY OF THE INVENTION

Broadly stated the present invention comprises a method for producing para alkylated primary aromatic amines by alkylating a primary aromatic amine with an olefin in the presence of an acid activated acidic clay, preferably a montmorillonite clay, at temperatures in the range of about 100° C. to about 400° C.

DETAILED DESCRIPTION OF THE INVENTION

The primary aromatic amines alkylated in accordance with the invention are those having a hydrogen on the aromatic nuclear carbon in the position para to the amine moiety on the aromatic ring. In the present invention it is preferred that the primary aromatic amine be a phenylamine and more preferably be aniline.

In the process of the invention the olefin employed may be an aliphatic or cyclic olefin having from 2 to about 8 carbon atoms and preferably from 2 to 4 carbon atoms. The olefins of particular interest are ethylene, propylene, butylene and isobutylene with isobutyl being especially preferred.

The catalyst according to the invention is an acid treated montmorillonite clay that has not been rendered neutral but instead has a residual acidity. Indeed the residual acidity is preferably about 3 but can be greater than 3, for example from about 3 to about 6. Such catalysts are commercially available.

The ratio of olefin to amine used in the process of the invention typically will be about 1:1 to less than 1:1, for example, from about 1:1 to about 0.3:1, and preferably about 0.7:1.

The amount of catalyst employed is not critical and typically will be in the range of from about 1 to about 10 wt % based on the weight of aromatic amine.

The reaction is carried out at temperatures ranging from about 50° C. to about 400° C. and preferably in the range of 200° C. to 300° C. Elevated pressures typically are employed, for example, from about 6.89 mPa (1000 psi) to about 68.9 mPa (10,000 psi). Conveniently the reaction may be conducted at lower pressures, for example, in the range of 1378 kPa to 2067 kPa by adding the olefin to the heated amine and catalyst over an extended period. For example, the olefin may be added slowly or in increments to either the liquid or vapor phase in the reactor extending the addition from 10 minutes up to about 2.5 hours. In any event it is preferred to continue the heating after the completion of the olefin addition for a time sufficient to convert at least 85% and preferably greater than about 90% of the amine whereby increased yields and high selectivity of the para-alkylated species is obtained.

The advantages of the invention will be illustrated by the following examples.

EXAMPLE

Two runs were conducted each using the procedure described herein.

A slurry of 2000 g of phenylamine and 200 g of an acid activated acidic montmorillonite catalyst sold as F-22 by Englehard Chemicals Inc. and having a residual acidity of 3 was introduced into a reactor via a sample line by applying a slight vacuum to the reactor. The reactor was stirred (950 RPM), purged several times using 3.445 mPa (500 psi) nitrogen and then heated to 250° C. The autogeneous pressure of phenylamine at these conditions was about 430 kPa (60 psi). Isobutylene was introduced into the reactor, in run-1 directly into the liquid and in run-2 into the vapor space above the liquid. In each instance the isobutylene was added in about 10% increments over a period of 2 hours 15 minutes in run 1 and 2 hrs and 27 minutes in run 2. Samples were withdrawn from the reactor at 2, 4 and 6 hour intervals after all the isobutylene was added. The samples were filtered to remove the catalyst and then subjected to G.C. analysis. The results obtained are given in Table 1.

TABLE 1

ALKYLATION OF ANILINE WITH ISOBUTYLENE AT 250° C.
(F-22-Montmorillonite Catalyst - Engelhard)

FEED

| Aniline | 2000 g | 21.5 moles |
|---|---|---|
| Clay | 200 g | |
| Isobutylene | 845 g | 15 moles |

Mole Ratio: Isobutylene/Aniline = 0.7

| | | Aniline | Product Distribution %[2] | | | |
|---|---|---|---|---|---|---|
| Run I.D. | Time, Hr | Conv. (%)[1] | N-C4 | o-C4 | p-C4 | Di-Substit |
| Run 1-1 | 2 | 71.5 | 0.3 | 2.8 | 92.8 | 4.1 |
| Run 1-2 | 4 | 88.5 | 0.2 | 1.6 | 94.7 | 3.5 |
| Run 1-3 | 6 | 90.3 | 0.2 | 1.6 | 94.4 | 3.8 |
| Run 2-1 | 2 | 91.6 | 0.2 | 1.4 | 94.8 | 3.6 |
| Run 2-2 | 4 | 94.6 | 0.2 | 2.0 | 93.8 | 4.0 |
| Run 2-3 | 6 | 92.4 | 0.2 | 1.8 | 94.2 | 3.9 |

[1]Based on theoretical moles of aniline for a mono alkylation reaction.
[2]Based on moles of aniline reacted.

What is claimed is:

1. A method for selectively producing para-alkylated primary aromatic amines comprising reacting a primary aromatic amine reactant having a hydrogen in the para position with an olefin in the presence of an acid activated montmorillonite clay having a residual acidity of from about 3 to about 6, the reaction being conducted in a reactor at a temperature in the range of about 50° C. to about 400° C. wherein the olefin is introduced into the vapor space in the reactor above the primary aromatic amine and acid activated clay and wherein greater than about 90% of the amine is converted into alkylated primary aromatic amine and wherein the amount of para-alkylated primary aromatic amine produced is at least 93.8% based on the moles of primary aromatic amine reacted.

2. The method of claim 1 wherein the olefin has from 2 to about 8 carbon atoms.

3. The method of claim 2 wherein the primary aromatic amine which is reacted with the olefin is aniline.

4. The method of claim 1 wherein the olefin is isobutylene.

5. A method for producing para-tertiary butyl aniline comprising:
providing a reactor with a slurry of aniline and an acid activated montmorillonite clay catalyst having a residual acidity of from about 3 to 6;
heating the slurry to a temperature in the range of about 50° C. to about 400° C.;
introducing isobutylene into the vapor space in the reactor over the slurry of aniline and acid activated montmorillonite clay over a period of time, the ratio of isobutylene to aniline being in the range of 1:1 to 0.3:1; and
continuing the heating for a time sufficient to convert at least 90% of the aniline to tertiary butyl aniline and wherein the para-tertiary butyl aniline is produced in an amount which constitutes at least 93.8% of the tertiary butyl anilinqproduct based on the moles of aniline reacted.

6. The method of claim 5 wherein the clay has a residual acidity of about 3 and wherein the ratio of isobutylene to aniline is about 0.7:1.

7. The method of claim 1 wherein the reaction is conducted in the reactor at a temperature in the range of about 200° C. to about 300° C.

8. The method of claim 5 wherein the slurry is heated to a temperature in the range of about 200° C. to about 300° C.

* * * * *